United States Patent [19]

Nagai et al.

[11] Patent Number: 5,051,133

[45] Date of Patent: Sep. 24, 1991

[54] GELATINIZED CEREAL FLOURS AND PROCESS FOR THEIR PRODUCTION

[75] Inventors: Tadashi Nagai, Tokyo; Yayoi Nademoto, Osaka, both of Japan

[73] Assignee: Suntory Limited, Osaka, Japan

[21] Appl. No.: 448,297

[22] Filed: Dec. 11, 1989

[30] Foreign Application Priority Data

Dec. 12, 1988 [JP] Japan .............................. 63-313656
Mar. 29, 1989 [JP] Japan .................................. 1-77913

[51] Int. Cl.⁵ ............................................ C08B 30/00
[52] U.S. Cl. ....................................... 127/65; 127/69; 127/71; 426/573; 426/578; 426/661; 536/102
[58] Field of Search ................... 127/71, 69; 426/573, 426/578, 661; 536/102; 252/315.3

[56] References Cited

U.S. PATENT DOCUMENTS 3,928,321 12/1975 Tessler ................................ 536/103
4,020,272 4/1977 Tessler ................................ 536/107
4,510,166 4/1985 Lenchin et al. ..................... 426/565

FOREIGN PATENT DOCUMENTS 0581622 11/1976 Japan .
63-49050 3/1988 Japan .
63-49054 3/1988 Japan .

*Primary Examiner*—Theodore Morris
*Assistant Examiner*—P. L. Hailey
*Attorney, Agent, or Firm*—Cushman, Darby & Cushman

[57] ABSTRACT

Porous modified gelatinized cereal flour that has high swelling property in cold water, high solubility and good digestability and which is useful as a fragrance adsorbent or an emulsion stabilizer. Also disclosed is a process for producing such porous gelatinized cereal flour which comprises adding water to a cereal flour containing starch as a principal component, heating said flour to gelatinize it, adding an alcohol to the gelatinized flour, and freeze-drying the same.

1 Claim, 2 Drawing Sheets

GELATINIZED STARCH OF EX.1
(8000 rpm x 1 min)

GELATINIZED STARCH
(8000 rpm x 1 min)

GELATINIZED STARCH OF EX.1
(1300 rpm x 3 min)

GELATINIZED CEREAL FLOURS AND PROCESS FOR THEIR PRODUCTION

BACKGROUND OF THE INVENTION

The present invention relates to a process for producing modified gelatinized cereal flours, particularly to a process for producing a gelatinized cereal flour having a porous structure by adding an alcohol to a gelatinized cereal flour and freeze-drying the mixture. The present invention also relates to the porous gelatinized cereal flour thus produced. Further, the present invention relates to a fragrance adsorbent and an emulsion stabilizer that are composed of a gelatinized cereal flour.

On account of their unique polymer characteristics, native and processed starches are used in a broad range of applications including food use. In particular, gelatinized starches or processed starches that are manufactured by suspending native starches in water and then drying by heating them have long been used in various applications since they have good utility and storage stability and because they can be produced by simple techniques using drum dryers and other readily available devices. However, the recent changes in people's life style, particularly in the foods they eat, have caused corresponding changes in the form of various foodstuffs or raised a need for the development of new functional materials in various fields, and it has become increasingly difficult to obtain a desired product merely by utilizing the properties of native starches and conventional processed starches including gelatinized starches.

Gelatinized starches have markedly different properties depending upon the process of their production or the starting materials from which they are produced. Thus, gelatinized starches that are adapted for various uses can be manufactured by selecting proper production process, conditions and starting materials. With a view to acquiring new properties by making use of this advantageous nature of gelatinized starches, various methods for their production have been developed. It has, for example, been reported that when raw starch is converted to a gelatinized form in an aqueous alcohol solution under pressure, gelatinized starch that almost completely retains the shape of granules in the raw starch and which resists agglomeration when dissolved in water can be obtained (Japanese Patent Public Disclosure No. 63-49054). A problem with the conventional gelatinized starch is that when it is dissolved in water, agglomerates are often formed, thus making it unsuitable for use as a constituent material of bean-jam cakes. In order to solve this problem, it has been proposed that a gelatinized cereal flour such as kanbai-ko (gelatinized glutinous rice flour) be mixed with water and an alcohol and dried with heat (Japanese Patent Public Disclosure No. 63-49050). Since water penetration into the treated cereal flour is suppressed, it will not experience rapid swelling upon water absorption, thereby resisting agglomeration. The use of an oxidized starch as an emulsion stabilizer after enzyme treatment has also been reported (Japanese Patent Publication No. 58-1622).

A method of suspending starch in water, heating the suspension and freeze-drying it in vaccum has drawn increasing attention as a technique for producing processed starches having new properties. The starch thus produced has been reported to have a greater ability to absorb oils and other fluids than the raw starch. However, various process conditions have to be considered before drying methods such as freeze-drying can be effectively utilized.

Even if freeze-drying is directly applied as a drying method instead of thermal drying for a mixture of gelatinized cereal flour with water and an alcohol, a fine structure cannot be effectively created in the surface of starch granules and a desired porous structure is not attainable.

SUMMARY OF THE INVENTION

It is therefore an object of the present invention to provide a process for producing a modified gelatinized cereal flour that has a porous structure with a sufficiently increased specific surface area to insure good swelling in cold water, solubility and digestability compared to prior art gelatinized cereal flours and that can be used as an emulsion stabilizer or an adsorbent for volatile materials.

Another object of the present invention is to provide a porous gelatinized cereal flour.

Still another object of the present invention is to provide a fragrance absorbent and an emulsion stabilizer that are composed of a gelatinized cereal flour.

DETAILED DESCRIPTION OF THE INVENTION

Figure 1:
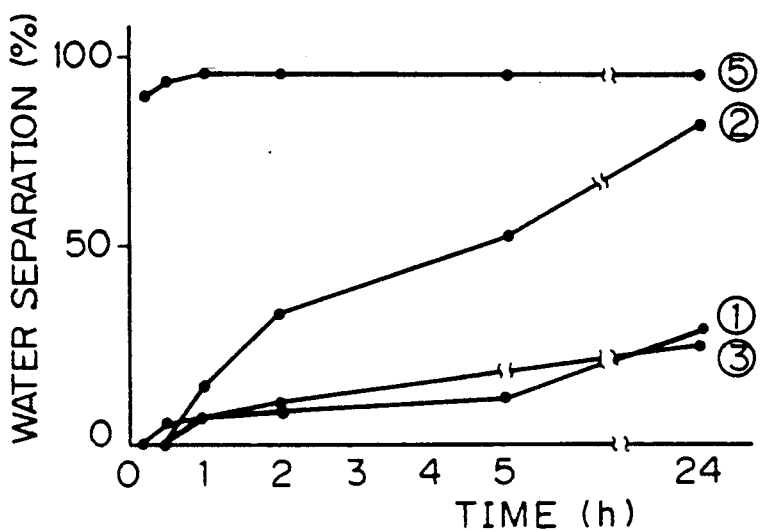
FIG. 1 is a graph showing differences in emulsion stability according to the conditions of agitation.

The present inventors conducted intensive studies on various methods for producing gelatinized starches in order to obtain gelatinized cereal flours having improved properties. As a result, they found that a modified gelatinized cereal flour that was porous and which had improved properties such as high swelling and solubility could be produced by first adding water to a cereal flour chiefly composed of starch, heating the mixture to gelatinize it, then adding an alcohol to the gelatinized mixture, and finally freeze-drying it. The present invention has been accomplished on the basis of this finding.

The process of the present invention comprises the steps of suspending raw starch or a cereal flour chiefly composed of starch in water, heating the suspension to have the starch fully converted to a gelatinized form, adding an alcohol to said gelatinized starch, and freeze-drying the same.

The process of the present invention is described below in detail. It starts with suspending raw starch or a starch-based cereal flour in water. Then, the suspension is heated and held at a temperature not lower than the gelatinization temperature of the starch for a sufficient period to insure that the starch in the suspension is completely converted to a gelatinized form. An alcohol is added to the resulting liquid which contains the gelatinized starch, and the whole mixture is rendered to become homogeneous. The alcohol may be added while the gelatinized starch is still hot or after it has become cold. Preferably, the alcohol is added while the gelatinized starch is still hot, and more preferably, it is slowly added with stirring effected to avoid inhomogeneity before the temperature becomes lower than the point at which starch gelatinizes. Subsequently, the mixture is cooled to room temperature as required and freeze-dried to remove water and the alcohol. The freeze-dried gelatinized cereal flour is ground to powder.

The gelatinized cereal flour thus obtained has a well developed fine surface structure and, because of its porous structure, it has improved properties, particularly in specific surface area, specific volume and solubility.

The ratio at which the starting cereal flour is mixed with water will depend on various factors such as the type of starch contained in the starting cereal flour and the shape of starch granules. Preferably, 200–5,000 parts by weight of water is mixed with 100 parts by weight of the starting cereal flour. The amount of alcohol to be added will vary with the type of gelatinized starch to be obtained; it is usually added in an amount of 5–40 vol% of the water used to gelatinize the starch. The degree of porosity will also vary, particularly with the type of alcohol used; for example, if ethanol is used, the amount of ethanol ranges from 5 to 40 vol%, preferably from about 17 to about 40 vol%. Generally, if less than 5 vol% of alcohol is added, desired modification is not attainable, and even if more than 40 vol% of alcohol is added, there is no further improvement in the modification by creation of a porous structure.

The freeze-drying method that is used in the present invention is by no means a special technique and it is commonly employed in the food industry.

The size of particles is generally correlated with their surface area but in the case of the gelatinized starch produced by the present invention, the particles have a satisfactorily porous structure and their size will have no substantial effect on the surface area if they are of an ordinary size. Hence, any method of grinding such as ball milling that is conventionally employed in the manufacture of gelatinized starches may be used in the present invention. The gelatinized starch may generally be pulverized into particles of a size ranging from 10 microns to several times that number of millimeters but this range may be properly adjusted in accordance with its object and use.

The cereal flour chiefly composed of starch that can be used in the process of the present invention is not limited in any particular way with respect to such factors as type and grain size. It may contain minor amounts of proteins, oils and other components as long as it contains starch as the principal component. Starch powders purified from such cereal flours or mixtures thereof may also be used. Exemplary cereal flours or starches are those which originate from potatoes, sweet potatoes, tapioka, corn, wheat and rice.

The alcohol to be used in the process of the present invention is preferably selected from among hydrophilic alcohols such as methyl alcohol, ethyl alcohol and propyl alcohol, with propyl alcohol and ethyl alcohol being particularly preferred. If the only factor that need be considered is the modification of starch granules by creating a porous structure, propyl alcohol is the most preferred. However, if the process of the present invention is to be used in the food industry, ethyl alcohol would be the best.

The gelatinized cereal flour of the present invention is more porous than those gelatinized cereal flours and starches which are obtained by the prior art methods. Typically, it has a specific surface area of at least about 1 $m^2/g$, preferably at least about 3 $m^2/g$, more preferably at least 5 $m^2/g$, and most preferably at least 10 $m^2/g$. Thus, the gelatinized cereal flour of the present invention has a large specific surface area and specific volume, contributing improved properties such as high solubility. Such improved properties enable said gelatinized cereal flour to find utility in various applications.

In order to use the gelatinized cereal flour of the present invention as an adsorbent of fragrances, one only need grind said flour into particles, which are then brought into contact or mixed with a desired fragrance by any suitable method. Hence, the fragrances that can be adsorbed are not limited to any particular type and they may be either volatile or oily. Depending on the nature of an adsorbate, the vapors of volatile materials that are adsorbed can be readily desorbed by heating the gelatinized cereal flour.

In order to use the gelatinized cereal flour of the present invention as an emulsion stabilizer, one only need grind said flour into particles, mix them with an oil (or water), add water (or oil), and disperse them by any suitable method such as agitation.

The gelatinized cereal flour obtained by the method of the present invention has a satisfactorily porous structure, which imparts such desirable properties to the flour as exemplified by good solubility, digestability, swelling, inflatability and a great capacity to adsorb fluids and volatile materials. Because of these properties, the gelatinized cereal flour can be extensively used in food industry as cake mixes having various flavors adsorbed thereon as agents to improve the palatability of expandable foods such as snacks and cream puffs, as fragrances (slow-release materials), decolorants, deodorants, and as powder bases that are to be used in making powders from fluid materials such as flavors, spices, dyes and oils. The gelatinized cereal flour of the present invention also has improved emulsion stability and thickening ability and hence can be used effectively as an emulsion stabilizer or thickener in low-calorie emulsified fats or oils, mayonnaise, dressings, sauces, etc. The applicability of this flour is not limited to the food industry and its properties may be fully exploited when it is used as a liquid or gas adsorbent or deodorant or as a column packing agent.

As described above, the process of the present invention enables the production of a porous gelatinized cereal flour from cereal flours that contain starch as a chief component. Compared to the porous gelatinized starches that were previously produced by the conventional freeze-drying method, the gelatinized cereal flour produced by the method of the present invention is improved not only in such aspects as solubility, swelling property and the ability to adsorb fragrances and fluids but also in effectiveness as an emulsion stabilizer.

EXAMPLE 1

A hundred parts by weight of potato starch (11% moisture) was mixed with 600 parts by weight of water and slurried. The slurry was left to stand on a hot water bath until the starch was fully converted to gelatinized form (as evidenced by the clarity of the slurry). While the gelatinized starch was still hot, 200 parts by volume of ethanol was added with stirring effected to homogeneity and the mixture was cooled to room temperature. The cooled mixture was freeze-dried to a water content of about 6%, whereupon the desired porous gelatinized starch was obtained.

COMPARATIVE EXAMPLE 1

A hundred parts by weight of potato starch (11% moisture) was mixed with 600 parts by weight of water and slurried. The slurry was left to stand on a hot water bath until the starch was fully converted to gelatinized form (as evidenced by the clarity of the slurry). The resulting gelatinized starch was cooled to room temperature and freeze-dried to a water content of about 6%.

EXAMPLE 2

A hundred and forty parts by weight of wheat flour (10% moisture) was mixed with 600 parts by weight of water and the mixture was left to stand on a boiling water bath until the starch was fully converted to gelatinized form. While the gelatinized starch was still hot, 200 parts by volume of ethanol was added with stirring effected to homogeneity and the mixture was cooled to room temperature. The cooled mixture was freeze-dried to a water content of about 9.5%, whereupon the desired porous gelatinized wheat flour was obtained.

COMPARATIVE EXAMPLE 2

A hundred and forty parts by weight of wheat flour (10% moisture) was mixed with 600 parts by weight of water and the mixture was left to stand on a boiling water bath until the starch was fully converted to gelatinized form. The resulting gelatinized starch was cooled to room temperature and freeze-dried.

EXAMPLE 3

A hundred parts by weight of rice flour (10% moisture) was mixed with 500 parts by weight of water and the mixture was left to stand on a boiling water bath until the starch was fully converted to gelatinized form. While the gelatinized starch was still hot, 100 parts by weight of ethanol was added with stirring effected to homogeneity and the mixture was cooled to room temperature. The cooled mixture was freeze-dried to a water content of about 12%, whereupon the desired porous gelatinized rice flour was obtained.

COMPARATIVE EXAMPLE 3

A hundred parts by weight of rice flour (10% moisture) was mixed with 500 parts by weight of water and the mixture was left to stand on a boiling water bath until the starch was fully converted to gelatinized form. The resulting gelatinized starch was cooled to room temperature and freeze-dried.

The gelatinized starches obtained in Examples 1-3 and Comparative Examples 1-3 were compared with respect to their properties and functional characteristics.

EXPERIMENT 1

Changes in Physical Properties upon Modification

In order to investigate the changes that occurred in physical properties of the samples, their specific surface areas and specific volumes were measured.

|  | Specific surface area ($m^2/g$) | Specific volume (ml/g) |
| --- | --- | --- |
| Untreated potato starch | 0.15 | 1.10 |
| gelatinized starch of | 0.25 | 2.39 |
| Comparative Example 1 | | |
| gelatinized starch of Example 1 | 22.7 | 2.83 |
| Untreated wheat flour | 0.64 | 1.52 |
| gelatinized starch of Comparative Example 2 | 0.75 | 1.56 |
| gelatinized starch of Example 2 | 3.73 | 2.34 |
| Untreated rice flour | 0.56 | 1.32 |
| gelatinized starch of Comparatie Example 3 | 0.66 | 1.97 |
| gelatinized starch of Example 3 | 3.34 | 2.63 |

As is clear from this table, the samples of gelatinized starch prepared in Examples 1-3 by performing freeze-drying after addition of alcohols had greater values of specific surface area and volume and hence were more porous than the samples prepared in Comparative Examples 1-3 merely by performing freeze-drying without adding alcohols.

EXPERIMENT 2

Behavior in Aqueous Solutions

In order to evaluate the degree of swelling and solubility, a 500-mg sample was shaken in 25 ml of water at 37° C. for 24 hours and centrifuged at 3,000 rpm for 40 minutes. The content of starch in the supernatant was measured by the phenol-sulfuric acid method and the weight of the precipitate was thereafter measured. Solubility was expressed in terms of the proportion of starch dissolved in water, and the degree of swelling was expressed in terms of the weight of precipitate divided by the dry weight of starch undissolved in water. Digestability was evaluated by the following procedure: a solution containing 300 mg of sample was mixed with $\alpha$-amylase in an amount of 0.01% of the sample weight; the mixture was shaken at 37° C. for 24 hours and centrifuged at 1,000 rpm for 20 minutes; the supernatant was dried and its weight was measured.

|  | Solubility (%) | Degree of swelling | Digestability (mg) |
| --- | --- | --- | --- |
| Untreated potato starch | 0.04 | 2.22 | 0.90 |
| gelatinized starch of Comparative Example 1 | 1.27 | 8.33 | 43.0 |
| gelatinized starch of Example 1 | 29.2 | 30.0 | 53.0 |

As is clear from this table, the gelatinized potato starch prepared in Example 1 by performing freeze-drying after addition of an alcohol was 20 times as soluble as the sample prepared in Comparative Example 1 merely by performing freeze-drying without adding an alcohol. The degree of swelling of the sample of Example 1 was 4 times as high as the comparative example. The difference in digestability between the two samples was negligible. This attests to the fact that the gelatinized starch of the present invention was more porous than the comparative sample.

EXPERIMENT 3

Inflatability:

Dough consisting a mixture of a sample and water was dropped on a hot plate (230° C.) and pressed from above with another hot plate (200° C.). Since the dough spread in a substantially circular form, its thickness and diameter was measured at three points with a vernier caliper and its volume was calculated.

|  | Sample:water | Volume per mg of dough (mm³/mg) | Volume per mg of sample (mm³/mg) |
|---|---|---|---|
| Untreated potato starch | 1:1 | 8.45 | 4.23 |
| gelatinized starch of Comparative Example 1 | 1:2 | 5.53 | 3.69 |
| gelatinized starch of Example 1 | 1:2 | 10.13 | 6.75 |

As for potato starch, the gelatinized starch prepared merely by performing freeze-drying without adding an alcohol was more inflatable than the untreated sample but less inflatable than the sample prepared by performing freeze-drying after adding an alcohol. This would be because of the increase in the amount of air that was incorporated into the starch.

EXPERIMENT 4

Adsorption of Fragrance:

Each of the samples was left to stand for 1 week in an atmosphere filled with a commercial coffee flavor and thereafter stored in a vial at room temperature. The degree of adsorption and dissipation of the flavor from each sample was checked immediately after adsorption, 1 week and 3 weeks after the adsorption. The amount of flavor detected by gas chromatography (GC) was expressed by peak height.

|  | Amount of flavor | | Organoleptic evaluation | |
|---|---|---|---|---|
|  | Immediately after adsorption | 3 weeks | Immediately after adsorption | 1 and 3 weeks |
| Untreated potato starch | 2555 | 1108 | almost odorless | 1 wk: almost odorless  3 wk: almost odorless |
| gelatinized starch of Comp. Example 1 | 28962 | 6219 | weak coffee flavor | 1 wk: the sweet aroma of coffee attenuated  3 wk: almost odorless |
| gelatinized starch of Example 1 | 37335 | 48863 large tailing | strong coffee flavor | 1 wk: strong coffee flavor  3 wk: strong coffee flavor |
| Untreated wheat flour | 2818 | undetectable | almost odorless | 1 wk: almost odorless  3 wk: almost odorless |
| gelatinized starch of Example 2 | 106658 | 105782 | sweet coffee aroma | 1 wk: strong note of sweet aroma  3 wk: weak but distinct note of coffee aroma |
| Untreated rice flour | 2658 | undetectable | slight acrid smell | 1 wk: almost odorless  3 wk: almost odorless |
| gelatinized starch of Comp. Example 3 |  |  | weak coffee aroma | 1 wk: sweet aroma persisted  3 wk: almost odorless |
| gelatinized starch of Example 3 | 120136 | 110106 | strong coffee aroma | 1 wk: coffee aroma and sweetness persisted  3 wk: no coffee aroma persisted |

The data in the above table shows that compared to the comparative samples, the starches prepared in Examples 1-3 by performing freeze-drying after addition of an alcohol not only adsorbed a fragrance effectively but also retained it for a prolonged period of time. Wheat and rice flours were inherently capable of adsorbing high-boiling point components because they contained proteins and this capability would be enhanced by creating a porous structure in the grains.

EXPERIMENT 5

Adsorption of Fluids

Each of the samples was evaluated for their ability to adsorb water, alcohol and soybean oil. Filter paper was set on the inside surface of a funnel and each of the fluids to be tested was poured over each sample placed on the filter paper. When the test fluid no longer dripped down from the bottom of the funnel, the weight of each sample was measured.

|  | Adsorption (g) per gram of sample | | |
|---|---|---|---|
|  | water | ethanol | soybean oil |
| Untreated potato starch | 1.26 | 0.33 | 0.41 |
| gelatinized starch of Comparative Example 1 | 6.79 | 1.15 | 1.67 |
| gelatinized starch of Example 1 | 14.05 | 1.35 | 1.94 |
| Untreated wheat flour | 0.88 | 0.72 | 0.70 |
| gelatinized starch of Comparative Example 2 | 4.82 | 1.15 | 1.08 |
| gelatinized starch of Example 2 | 5.75 | 1.53 | 2.04 |
| Untreated rice flour | 1.83 | 0.42 | 0.68 |
| gelatinized starch of Comparative Example 3 | 5.00 | 1.40 | 1.55 |
| gelatinized starch of Example 3 | 7.01 | 1.50 | 1.85 |

The above results show that compared to the gelatinized starches that were prepared merely by performing freeze-drying without adding an alcohol, those which were prepared in Examples 1-3 by performing freeze-drying after addition of an alcohol had great ability to adsorb various fluids.

When 5 g of the potato starch in gelatinized form that was prepared in Example 1 was mixed with 5 g of a commercial coffee oil, a flavor powder could be obtained. However, only an agglomerate was obtained when 5 g of the potato starch in gelatinized form that was prepared in Comparative Example 1 merely by performing freeze-drying without adding an alcohol was mixed with 5 g of a commercial coffee oil.

EXPERIMENT 6

Oil Retention

The gelatinized starch prepared in Example 1 was mixed at various proportions with soybean oil and its oil retaining ability was investigated.

| | \multicolumn{7}{c}{Proportions of soybean oil and sample} | | | | | | |
|---|---|---|---|---|---|---|---|
| | 3:1 | 2:1 | 3:2 | 1:1 | 2:3 | 1:2 | 1:3 | 1:4 |
| Starch of Example 1 | | | Δ | ○ | ○ | ⊙ | ⊙ | |
| Starch of Comparative Example 1 | | | | Δ | ○ | ○ | ⊙ | |
| "Pine Flow" | X | ○ | ⊙ | ⊙ | | | | |
| "Pine Star S" | | | | X | Δ | Δ | Δ | ○ |
| Anhydrous crystalline maltose | | | | X | X | Δ | ○ | ⊙ |

⊙: powder;
○: wet powder;
Δ: lumpy;
X: cream

"Pine Flow" (decomposed starch used as a base for producing powdered fats or oils) and "Pine Star S" (decomposed starch used as an extender or emulsion stabilizing aid) were commercially available from Matsutani Chemical Ind. Co., Ltd., and anhydrous crystalline maltose was available from Hayashibara Biochemical Laboratories Inc. The gelatinized starch of Example 1 had a significant oil retaining ability although it was not as effective as "Pine Flow".

EXPERIMENT 7

Emulsion Stability

The emulsion stabilizing ability of the gelatinized starches prepared by the method of the present invention was investigated by the following procedure. A vessel was charged with 100 ml of water, 100 ml of soybean oil and 1 g of a powdered sample and shaken with a stirrer ("TK Auto Homomixer" of Tokushu Kika Kogyo Co., Ltd. which was also employed in subsequent experiments) at 5,000 rpm for 2 minutes to form a water-oil emulsion. This emulsion was left to stand to examine how it would separate into oil and water. The changes in the proportions of the two phases were expressed in terms of percentage. Hence, the proportion of the emulsion can be calculated by subtracting the proportions of the aqueous and oil phases from 100.

| Time (h) | Potato starch Untreated | Potato starch Comp. Ex. 1 | Potato starch Ex. 1 | Wheat flour Comp. Ex. 2 | Wheat flour Ex. 2 | Rice flour Comp. Ex. 3 | Rice flour Ex. 3 |
|---|---|---|---|---|---|---|---|
| 0.5 | oil 5 water 0 | oil 3 water 0 | oil 0 water 44 | oil 50 water 31 | oil 0 water 43 | oil 50 water 43 | oil 0 |
| 2 | oil 20 water 40 | oil 16 water 35 | oil 0 water 8 | oil 50 water 47 | oil 0 water 36 | oil 50 water 44 | oil 0 water 44 |
| 24 | oil 48 water 49 | oil 46 water 48 | oil 0 water 30 | oil 50 water 47 | oil 0 water 43 | oil 50 water 45 | oil 0 water 45 |

The above data shows that the gelatinized starches of Examples 1-3 had a greater emulsion stabilizing ability than the comparative samples prepared merely by performing freeze-drying without adding an alcohol.

Another experiment was conducted to find optimum conditions for stabilizing an oil-water emulsion using the gelatinized cereal flour prepared by the method of the present invention.

EXPERIMENT 8

Effects of the Conditions of Stirring on Emulsion Stability

One gram of the gelatinized starch prepared in Example 1 was mixed with 100 ml of soybean oil and the mixture was stirred lightly to homogeneity. Thereafter, 100 ml of water was added and the mixtures were stirred under various conditions to form emulsions. The emulsions were left to stand at room temperature and their stability was evaluated by observing the state of water separation. The following five conditions of stirring were employed: (1) 10,000 rpm × 1 minute; (2) 13,000 rpm × 3 minutes; (3) 8,000 rpm × 1 minute; (4) 5,000 rpm × 1 minute; and (5) the mixture of 1 g of the gelatinized starch of Example 1 and 100 ml of soybean oil was stirred at 10,000 rpm for 1 minute, and after addition of 100 ml of water, the mixture was stirred at 13,000 rpm for 2 minutes. The test results are shown in FIG. 1, from which one can see that emulsion stability varied with the conditions of stirring.

Figure 3A:
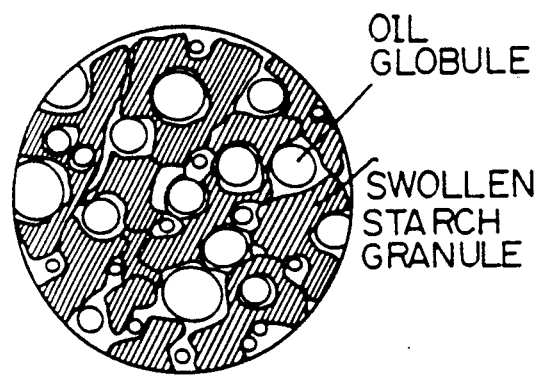
FIG. 3(A) shows the result obtained by stirring the gelatinized starch of example 1 under condition (3)
Figure 3C:
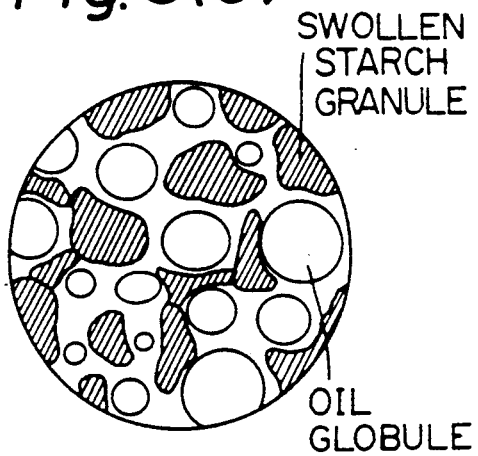
FIG. 3(C) shows the result obtained by stirring the comparative gelatinized starch under condition (3).
Figure 3B:
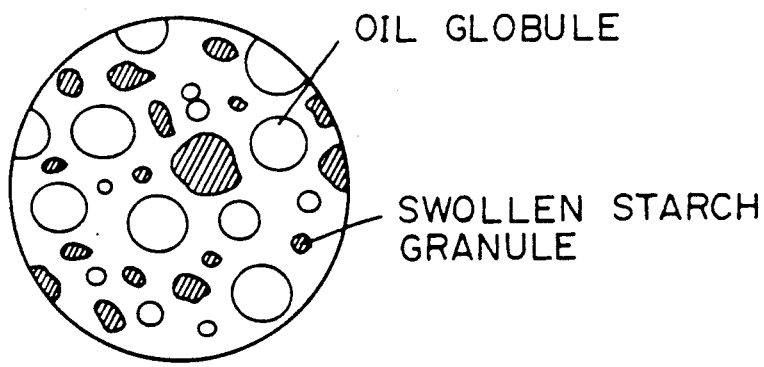
FIG. 3(B) shows the result obtained by stirring the gelatinized starch of example 1 on the condition (2)

In order to investigate the differences that would be caused in the state of emulsions depending upon the conditions of stirring and the type of gelatinized starch, microscopic observation was conducted and the results are shown in FIG. 3. FIG. 3(A) shows the result obtained by stirring the gelatinized starch of Example 1 under condition (3); FIG. 3(B) shows the result obtained by stirring the gelatinized starch of Example 1 under condition (2); and FIG. 3(C) shows the result obtained by stirring the comparative gelatinized starch under condition (3). Obviously, the emulsion using the gelatinized starch of Example 1 was stable since the starch granules swollen by water were interconnected in a network to prevent the coalescing of oil globules. On the other hand, the granules of the comparative gelatinized starch swelled insufficiently to exhibit the intended emulsion stabilizing effect. Even the gelatinized starch of Example 1 was not effective in stabilizing emulsions when it was stirred excessively to break the soft swollen granules into separate fragments.

EXPERIMENT 9

Comparison of Various Starches with Respect to Their Emulsion Stabilizing Effect:

The starches shown in the following table were stirred under condition (3) as in Experiment 8 and the stability of the resulting emulsions was evaluated.

| Sample | Specific surface area ($m^2/g$) |
|---|---|
| Raw starch | 0.15 |
| gelatinized starch | 0.60 |
| gelatinized starch of Example 1 | 22.7 |
| Starch freeze-dried in liquid nitrogen | 5.0 |
| "Pine Flow" | 0.58 |

Figure 2:
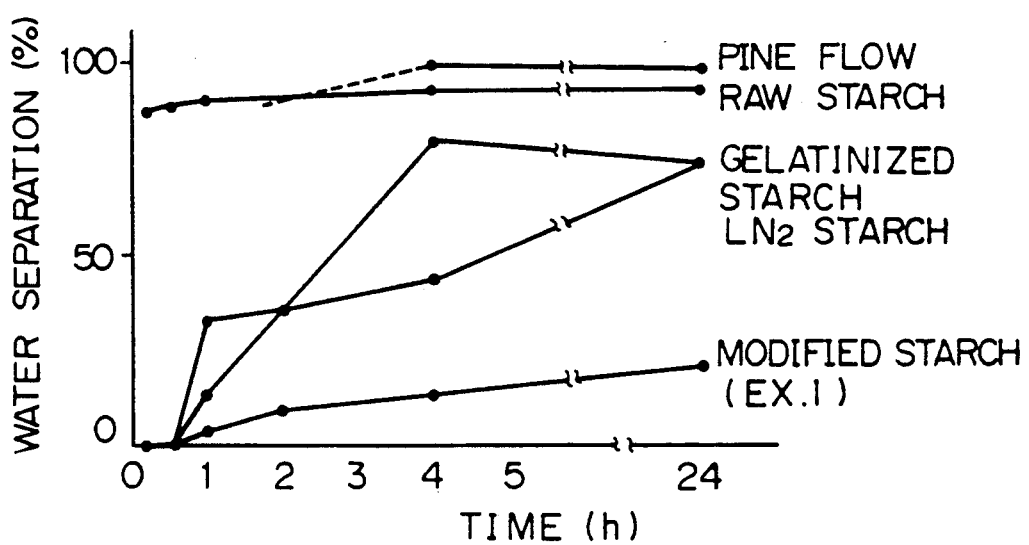
FIG. 2 is a graph showing differences in emulsion stability according to the type of starch used.

The results are shown in FIG. 2, from which one can see that the stability of emulsions was improved as the specific surface area of starch granules increased.

The results of Experiments 8 and 9 and the microscopic observations of the emulsions prepared in these experiments show that the excellent emulsion stabilizing ability of the gelatinized cereal flour of the present invention would be due to the fact that the granules of gelatinized starch having water or oil adsorbed thereon are dispersed in the emulsion.

EXPERIMENT 10

Emulsion Stability at Various Oil Contents

The effect of the proportions of water and oil on emulsion stability was investigated by the same method as employed in Experiment 8. The results are shown in the table that follows, in which the proportion of water that separated out after 24 hours is shown in the upper part of each box and the viscosity of the emulsion is shown in the lower part. The starch content (%) was determined by the following formula:

$$\text{Starch content (\%)} = \frac{\text{Amount of starch added (g)}}{\text{Total amount (ml)}} \times 100.$$

|  |  | gelatinized starch of Example 1 | | | gelatinized starch of Comparative Example 1 | | Raw starch | |
|---|---|---|---|---|---|---|---|---|
| Oil content (%) |  | 30 | 50 | 70 | 50 | 70 | 50 | 70 |
| Starch content (%) | 0 | 100 | 100 | 100 | 100 | 100 | 100 | 100 |
|  | 0.25 | 90 | 78 | 27 | 84 | 30 | 82 | 73 |
|  |  | 11.0 | 24.5 | 180.5 | 13.0 | 104.5 | 14.0 | 80.0 |
|  | 0.5 | 87 | 64 | 13 | 80 | 43 | 76 | 60 |
|  |  | 15.0 | 48.0 | 366.0 | 14.5 | 142.0 | 14.5 | 99.5 |
|  | 1.0 | 69 | 0 | 0 | 86 | 33 | 78 | 57 |
|  |  | 49.5 | 160.5 |  | 17.0 | 184.5 | 15.5 | 126.0 |

The above results show that compared to the comparative gelatinized starch and raw starch, the gelatinized starch of the present invention provided a higher viscosity when added in the same amount and that it achieved a greater thickening effect as the amount of its addition increased. This difference in thickening effect would be due to the differences in oil and water absorbing capability that originate from such factors as the specific surface area and fine porous structure of starch granules. The table also shows that the increase in thickening effect is accompanied by a corresponding improvement in emulsion stability.

EXPERIMENT 11

Comparison with Other Thickeners and Emulsion Stabilizers

The gelatinized starch of the present invention was compared with other thickeners and emulsion stabilizers and the effect of its porous structure on emulsion stability was investigated. Emulsions were prepared by the following procedures: a sample was dispersed or dissolved in water (or oil); after adding oil (or water), the mixture was stirred at 8,000 rpm for 1 minute and left to stand for 24 hours. The degree of water separation that occurred was observed. The samples tested were as follows: the gelatinized starch of Example 1; "Matsunorin SM" (gelatinized starch of Matsutani Chemical Ind. Co., Ltd.); "Farinex" (chemically processed starch of Matsutani Chemical Ind. Co., Ltd.); "Swely gel" (gelatinized starch of Oji National Co., Ltd.); "Echo Gum" (xanthan gum of Dai-Nippon Pharmaceutical Co., Ltd.); "Poem J-0021" (aliphatic acid ester of polyglycerin; Riken Vitamin Co., Ltd.); and "Emasol" (aliphatic acid ester of sorbitan; Kao Corp.) The results are shown in the following table.

|  | Amount added (%) | Viscosity | Emulsion type | Water separation (%) |
|---|---|---|---|---|
| gelatinized starch of Example 1 | 1.0 | 160.5 | O/W | 0 |
| Matsunorin SM | 0.7 | 148.0 | O/W | 72 |
| Farinex | 0.9 | 232.5 | O/W | 20 |
| Swely gel | 1.5 | 156.5 | O/W | 26 |
| Echo Gum | 0.06 | 223.0 | O/W | 0 |
| Poem | 1.0 | 24.5 | O/W | 64 |
| Emasol | 1.0 | 18.0 | O/W | 70 |

Conventional emulsifiers such as "Poem" and "Emasol" were capable of forming fine emulsions but at the same time, the emulsions soon experienced the separation of the aqueous phase.

EXAMPLE 4

Application to Oil Dressing

Using the gelatinized starch of the present invention, an oil dressing was prepared according to the recipe shown below.

| | |
|---|---|
| gelatinized starch of the present invention | 1.0 g |
| Water | 30.0 g |
| Apple vinegar | 27.0 g |
| Salad oil | 32.0 g |
| Sugar | 5.0 g |
| Sodium chloride | 2.0 g |

The viscosity of the dressing was 45 cps. Even when the addition of the salad oil was reduced, the desired viscosity could be attained by adding a small amount of the gelatinized starch of the present invention and yet the taste of the dressing was in no way affected ("Paceli SA 2" which was a commercial viscosity stabilizer produced by Matsutani Chemical Ind. Co., Ltd. had to be added in an amount of 8.0 g in order to attain the same level of viscosity). Thus, the gelatinized cereal flour of the present invention was also effective for products of low oil content.

EXPERIMENT 12

Measurements of Specific Surface Area

A hundred parts by weight of potato starch was mixed with 600 parts by weight of water and slurried. The slurry was left to stand on a hot water bath until the starch was fully converted to gelatinized form. While the obtained gelatinized starch was still hot, methanol, ethanol or 1-propanol was added in varying amounts (100, 150, 200 and 300 parts by volume) and the mixtures were well stirred to homogeneity, followed by cooling to room temperature. The cooled mixtures were freeze-dried at −20° C. The surface areas of the respective modified products were measured by the BET method through adsorption of nitrogen gas. The specific surface areas (m$^2$/g) were calculated for the respective concentrations of alcohols, and the results are shown in the following table. The gelatinized starch had a specific surface area of 0.6 m$^2$/g when no alcohol was added.

| Alcohol | Amount of alcohol added (parts by volume) | | | |
|---|---|---|---|---|
| | 100 | 150 | 200 | 300 |
| Methanol | 3.4 | 17.5 | 8.5 | 5.7 |
| Ethanol | 1.25 | 28.0 | 21.0 | 19.0 |
| l-propanol | 35.0 | 34.0 | 22.0 | |

As is clear from the above data, the specific surface area of gelatinized starch increased sharply when the addition of methanol or ethanol exceeded about 17 vol%. The specific surface area peaked at about 20 vol% and decreased gradually in the range exceeding about 33 vol%. When 1-propanol was added, specific surface areas exceeding about 20 m²/g were attained over the broad range of from about 5 to 40 vol%.

The data of Experiments 8-12, taken collectively, would indicate that compared to conventional starch systems, the gelatinized cereal flour of the present invention has such a large surface area that it wets easily with water to produce fully swollen starch granules which, when dispersed in an emulsion, will spread in the continuous phase to prevent the coalescing of oil globules and thereby stabilize the emulsion. Since the surface area of the gelatinized starch of the present invention can be adjusted by changing the conditions of modification within the range specified by the present invention, said starch is effective not only in stabilizing emulsions of various oil contents but also in adjusting their viscosities.

What is claimed is:

1. A process for producing a gelatinized cereal flour, which process comprises adding water to a cereal flour containing starch as a principal component, wherein water is added in an amount of 200-5,000 parts by weight per 100 parts by weight of the cereal flour heating said flour to gelatinize, adding an alcohol to the gelatinized flour, wherein the alcohol is added in an amount of 5-40 vol% of the volume of water and freeze-drying the same.

* * * * *